US00PP29557P2

(12) United States Plant Patent
Bergman

(10) Patent No.: US PP29,557 P2
(45) Date of Patent: Jul. 31, 2018

(54) ***CHRYSANTHEMUM* PLANT NAMED 'CIDZ0091'**

(50) Latin Name: *Chrysanthemum x morifolium*
Varietal Denomination: CIDZ0091

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,636

(22) Filed: Jul. 11, 2017

(51) Int. Cl.
*A01H 5/02* (2018.01)

(52) U.S. Cl.
USPC ..... Plt./286
CPC ..... *A01H 5/0255* (2013.01)

(58) Field of Classification Search
USPC ..... Plt./286
CPC ..... A01H 5/0255
See application file for complete search history.

*Primary Examiner* — Kent L Bell
(74) *Attorney, Agent, or Firm* — Dale Skalla

(57) ABSTRACT

A new *Chrysanthemum* plant named 'CIDZ0091' particularly distinguished by the purple and white bicolor, daisy-type inflorescences, excellent flower production, strong growth and spreading plant habit, and very uniform flowering with response time of 8 weeks when grown under short days.

1 Drawing Sheet

Latin name of the genus and species of the plant claimed: *Chrysanthemum x morifolium.*

Varietal denomination: 'CIDZ0091'.

BACKGROUND OF THE NEW PLANT

The present invention comprises a new *Chrysanthemum*, botanically known as *Chrysanthemum x morifolium*, and hereinafter referred to by the variety name 'CIDZ0091'.

'CIDZ0091' is a product of a planned breeding program. The new cultivar has purple and white bicolor, daisy-type inflorescences, excellent flower production, strong growth and spreading plant habit, and very uniform flowering with response time of 8 weeks when grown under short days.

'CIDZ0091' originated as a naturally occurring whole plant mutation discovered among flowering plants of 'B8040' growing in a greenhouse in Gilroy, Calif., in January 2014. The parent is the proprietary unpatented breeding line 'B8040', and having inflorescences of a dark purple hue under usual conditions, while it is similar to 'CIDZ0091' in all other characteristics.

The first act of asexual reproduction of 'CIDZ0091' was accomplished when vegetative cuttings were propagated from the initial selection in April 2014 in a greenhouse in Gilroy, Calif.

BRIEF SUMMARY OF INVENTION

Horticultural examination of plants grown from cuttings of the plant initiated August, 2014, and continuing thereafter, has demonstrated that the combination of characteristics as herein disclosed for 'CIDZ0091' are firmly fixed and are retained through successive generations of asexual reproduction.

'CIDZ0091' has not been observed under all possible environmental conditions. The phenotype may vary significantly with variations in environment such as temperature, light intensity and day length.

A Plant Breeder's Right for this cultivar has not been applied for. 'CIDZ0091' has not been made publicly available prior to the effective filing date of this application, notwithstanding any disclosure that may have been made less than one year prior to the effective filing date of this application by the inventor or another who obtained 'CIDZ0091' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0091' with colors being as true as possible with an illustration of this type.

Figure 1:
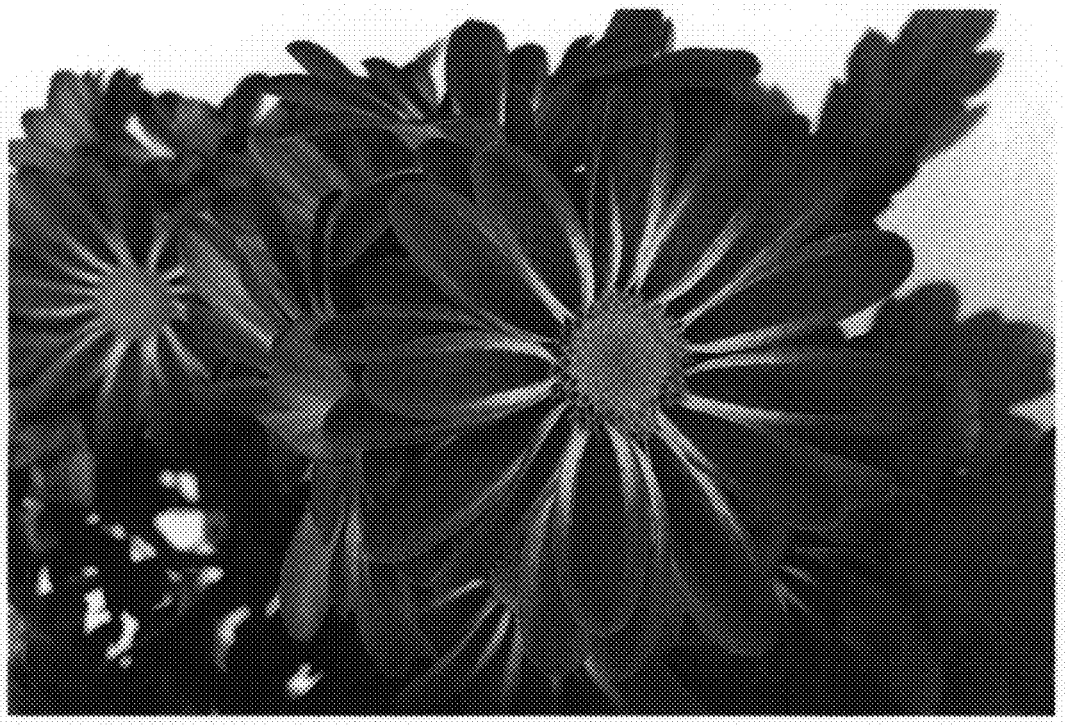
Figure 2:
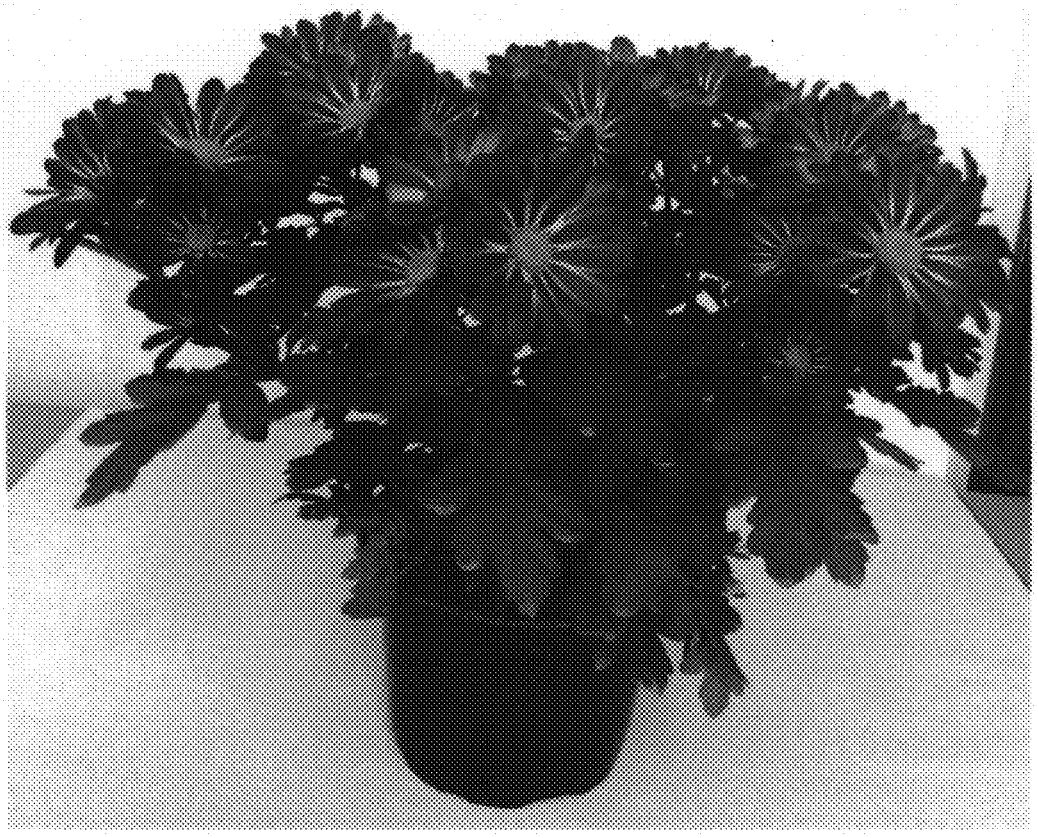

The photographic drawing shows in FIG. 1 a close-up view of the inflorescence of the new variety and in FIG. 2 a whole flowering plant grown in a greenhouse.

DETAILED BOTANICAL DESCRIPTION

The plant descriptions and measurements were taken indoors in Gilroy, Calif. in January 2017 on about 12 week old plants. Unrooted cuttings had been planted, 4 plants per pot, in 6 inch pots on Oct. 24, 2016. The plants were pinched and moved to short days on Nov. 14, 2016 to induce flowering.

The aforementioned photographs: FIGS. 1 and 2 were taken in Gilroy, Calif. in January 2017, and showing a plant from a trial, in which flowering had been induced by applying black cloth.

Color references are made to The Royal Horticultural Society Colour Chart (R.H.S.) 2001.

TABLE 1

DIFFERENCES BETWEEN THE NEW VARIETY 'CIDZ0091' AND A MOST SIMILAR VARIETY:

| | 'CIDZ0091' | 'YOAPPLE VALLEY' (U.S. Plant Pat. No. 21,420) |
|---|---|---|
| Plant height: | Taller | Shorter |
| Flower size: | Smaller | Larger |
| Flower quantity | Produces more flowers per plant | Produces less flowers per plant |

Plant:

*Form, growth and habit.*—Herbaceous pot-type, stems upright, freely branching, strong and moderately vigorous growth habit.

*Plant height.*—14.0-18.0 cm.

*Plant height (inflorescence included).*—17.0-23.0 cm.

*Plant width.*—30.0-34.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—RHS 138A.

*Mature, leaf color, upper surface.*—Between RHS 137A and 137B.

*Lower surface.*—RHS 137C.

*Length.*—7.3-7.7 cm.

*Width.*—6.0-6.7 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Bifid T-shaped hairs.

*Lower surface.*—Bifid T-shaped hairs.

*Color of veins, upper surface.*—RHS 138B.

*Color of veins, lower surface.*—RHS 138C.

*Pattern of veining.*—Palmate.

*Petiole color.*—RHS 138B.

*Length.*—1.7-2.0 cm.

*Diameter.*—0.3-0.5 cm.

*Texture.*—Bifid T-shaped hairs.

Stem:

*Quantity of main branches per plant.*—4-5.

*Color of stem.*—RHS 138B.

*Length of stem.*—14-18 cm.

*Diameter.*—0.3-0.5 cm.

*Length of internodes.*—0.5-1.7 cm.

*Texture.*—Bifid T-shaped hairs.

*Color of peduncle.*—RHS 138B.

*Length of peduncle.*—2.0-3.8 cm.

*Peduncle diameter.*—0.2 cm.

*Texture.*—Bifid T-shaped hairs.

Inflorescence:

*Type.*—Compositae type, solitary daisy-type inflorescences borne terminally above foliage, ray florets arranged acropetally on a capitulum.

*Quantity of short days to flowering (response time).*—8 weeks.

*Natural season flowering.*—Not determined on this variety.

*Quantity of inflorescences per plant.*—55-70.

*Lastingness of individual blooms on the plant.*—4 weeks.

*Fragrance.*—Slightly spicy.

Bud (just when opening/showing color):

*Color.*—Closest to RHS 71A overlain with RHS 155D.

*Length.*—1.0-1.5 cm.

*Width.*—1.0-1.2 cm.

*Shape.*—Oblate.

Immature inflorescence:

*Diameter.*—3.5-4.5 cm.

*Color of ray florets, upper surface.*—Closest to RHS 61A with 155D on lower half of the margins.

*Lower surface.*—Closest to RHS 61A overlain with 155D.

Mature inflorescence:

*Diameter.*—6.5-7.0 cm.

*Depth.*—2.0-2.5 cm.

*Total diameter of disc.*—1.2-1.5 cm.

*Receptacle color.*—RHS 145B.

*Receptacle height.*—0.3 cm.

*Receptacle diameter.*—0.4-0.5 cm.

Ray florets:

*Average quantity of florets.*—20-30.

*Color of ray florets, upper surface.*—Closest to RHS 60B with RHS 155D on the lower margin.

*Lower surface.*—Closest to RHS 60B overlain with RHS 155D.

*Length.*—2.3-2.8 cm.

*Width.*—0.8-1.0 cm.

*Shape.*—Eliptical.

*Apex shape.*—Acute.

*Margin.*—Entire.

*Texture, upper surface.*—Papillose.

*Lower surface.*—Papillose.

Disc florets:

*Average quantity of florets.*—110-130.

*Color of florets.*—RHS 8A basally fading to RHS 1D.

*Length.*—0.4-0.6 cm.

*Width.*—0.15-0.25 cm when open.

*Shape.*—Tubular, elongated.

*Apex shape.*—Acute, 5 pointed.

Phyllaries:

*Quantity.*—25-30.

*Color, upper surface.*—RHS 4A basally fading to RHS 145D.

*Lower surface.*—RHS 138A.

*Length.*—0.7-1.1 cm.

*Width.*—0.2-0.3 cm.

*Shape.*—Lanceolate.

*Apex shape.*—Acute.

*Base.*—Fused.

*Margins.*—Entire; slightly papery.

*Texture, upper surface.*—Glabrous.

*Lower surface.*—Bifid T-shaped hairs.

Reproductive organs:

*Pistil.*—1, found on both types of florets.

*Length.*—0.7 cm.

*Style color.*—RHS 155C.

*Style length.*—0.5 cm.

*Stigma color.*—RHS 17C.

*Stigma shape*.—Bi-parted.
*Ovary color*.—RHS 155C but more translucent.
*Stamens*.—4, found only on the disc florets.
*Color of filaments*.—RHS 155C.
*Length filaments*.—0.4-0.5 cm.
*Anther color*.—RHS 15A.
*Anther length*.—0.15 cm.
*Anther shape*.—Oval.
*Color of pollen*.—RHS 17B.
*Pollen amount*.—Sparse.
*Fertility/seed set*.—Has not been observed to date.
*Disease/pest resistance*.—Has not been observed to date.

What is claimed is:

1. A new and distinct variety of *Chrysanthemum* plant named 'CIDZ0091' substantially as illustrated and described herein.

* * * * *